US012690877B2

(12) United States Patent
Harris et al.

(10) Patent No.: US 12,690,877 B2
(45) Date of Patent: Jul. 28, 2026

(54) AUTOMATIC CRANIOTOMY AND BONEWORK VIA MILLING, FORCE SENSING, AND IMPEDANCE SENSING

(71) Applicant: Neuralink Corp., Fremont, CA (US)

(72) Inventors: John M. Harris, San Mateo, CA (US); Dalton James Colen, San Francisco, CA (US); Graydon J. Wilson, Milpitas, CA (US); Jamie N. Delton, Oakland, CA (US)

(73) Assignee: Neuralink Corp., Fremont, CA (US)

( * ) Notice: Subject to any disclaimer, the term of this patent is extended or adjusted under 35 U.S.C. 154(b) by 1023 days.

(21) Appl. No.: 17/537,212

(22) Filed: Nov. 29, 2021

(65) Prior Publication Data

US 2023/0165594 A1 Jun. 1, 2023

(51) Int. Cl.
*A61B 17/16* (2006.01)
*A61B 17/00* (2006.01)
(Continued)

(52) U.S. Cl.
CPC .......... *A61B 17/1695* (2013.01); *A61B 34/10* (2016.02); *A61B 90/30* (2016.02); (Continued)

(58) Field of Classification Search
CPC . A61B 17/1695; A61B 17/1626; A61B 17/32; A61B 17/1615; A61B 17/17; A61B 17/32002; A61B 17/1622; A61B 17/1624; A61B 17/1628; A61B 2017/1602; A61B 2017/00017; A61B 2017/00026; (Continued)

(56) References Cited

U.S. PATENT DOCUMENTS 5,599,142 A * 2/1997 Fujimoto ............... B23Q 15/12
408/6
2014/0222003 A1* 8/2014 Herndon ............ A61B 17/1622
606/80
(Continued)

OTHER PUBLICATIONS

"Hedlund et al., Automated craniotomy with impedance-sensitive skull curvature profiling, 2021, Optical Techniques in Neurosurgery, Neurophotonics, and Optogenetics, Proc. of SPIE vol. 11629, pp. 1-7" (Year: 2021).*

(Continued)

*Primary Examiner* — Sarah A Long
*Assistant Examiner* — Lauren Dubose
(74) *Attorney, Agent, or Firm* — Oblon, McClelland, Maier & Neustadt, L.L.P.

(57) ABSTRACT

Disclosed is a craniotomy milling system, which includes a computer numerical milling machine having a spindle configured to be positioned relative to a craniotomy location of a cranium of a patient and an end mill. The craniotomy milling system includes a controller for controlling the feed rate of the end mill. The craniotomy milling system includes an impedance measurement system and an axial force sensor. The craniotomy milling system includes a processor electrically coupled with a controller, the impedance measurement system, and the axial force sensor. The processor is configured to send a signal to the controller to change the feed rate of the end mill in response to a change in impedance or a change in axial force.

20 Claims, 9 Drawing Sheets

(51) Int. Cl.

| | |
|---|---|
| *A61B 34/10* | (2016.01) |
| *A61B 90/00* | (2016.01) |
| *A61B 90/30* | (2016.01) |
| *G05B 19/18* | (2006.01) |
| *G16H 20/40* | (2018.01) |

(52) U.S. Cl.

CPC ........... *G05B 19/182* (2013.01); *G16H 20/40* (2018.01); *A61B 2017/00017* (2013.01); *A61B 2017/00026* (2013.01); *A61B 2017/1602* (2013.01); *A61B 2034/105* (2016.02); *A61B 2090/064* (2016.02); *G05B 2219/37355* (2013.01)

(58) Field of Classification Search

CPC ... A61B 34/10; A61B 34/20; A61B 2090/064; A61B 2090/08021; A61B 2090/062; A61B 2090/3983; A61B 90/11; A61B 90/10; A61B 90/06; A61B 2034/107; A61B 2034/2055; A61B 17/1703; A61B 2090/103; A61B 2090/3937; A61B 90/14; A61B 90/30; G05B 19/182; G05B 19/18; G05B 2219/37355; G05B 2219/45145; G05B 2219/45129; G16H 40/63; G16H 30/40; G16H 50/70; G16H 20/40; G16H 70/20; B23B 2260/0482; B23B 2260/048; B23B 49/00

See application file for complete search history.

(56) References Cited

U.S. PATENT DOCUMENTS

| | | | | |
|---|---|---|---|---|
| 2016/0296242 | A1* | 10/2016 | Pak .................... | A61B 17/1695 |
| 2017/0113046 | A1* | 4/2017 | Fried ................. | A61N 1/36082 |
| 2019/0029697 | A1* | 1/2019 | Anderson .......... | A61B 17/1622 |
| 2020/0375695 | A1* | 12/2020 | Halter ................ | A61B 17/1633 |
| 2021/0330402 | A1* | 10/2021 | Abiven ................. | A61B 34/25 |
| 2022/0354510 | A1* | 11/2022 | Zhu .................... | A61B 17/1671 |

OTHER PUBLICATIONS

"Rynes et al., Assembly and operation of an open-source, computer numerical controlled (CNC) robot for performing cranial microsurgical procedures, 2020, Nature Protocols, vol. 15, pp. 1992-2023" (Year: 2020).*

"Ghanbari et al., Craniobot: A computer numerical controlled robot for cranial microsurgeries, 2019, Scientific Reports, vol. 9, pp. 1-13" (Year: 2019).*

Collins, D. (Aug. 27, 2021). What is an observer in motion control and how does it affect performance ?. Motion Control Tips. https://www.motioncontroltips.com/what-is-an-observer-in-motion-control-and-how-does-it-affect-performance/ (Year: 2021).*

Dai et al., Drilling Electrode for Real-Time Measurement of Electrical Impedance in Bone Tissues, Annals of Biomedical Engineering, Mar. 2014, pp. 579-588, vol. 42, No. 3, Tianjin, People's Republic of China.

Niesche et al., Smart Bioimpedance-Controlled Craniotomy: Concept and First Experiments, Journal of Engineering in Medicine, 2017, pp. 1-8 Sage, UK.

Acracut: https://www.acracut.com/perforators.html.

STRYKER The High Speed Drill Platform of Choice, Signature Portfolio, 2019, Kalamazoo, MI USA https://www.stryker.com/content/dam/stryker/nav-nse/products/-drive--Motor/resources/D0000006488%20Rev%20AA.3_SI180633%20NSE%20HSD%20SP%20Platform%20Brochure%20Rebrand%20v14_HIGH%20RES%20VIEWER%20SPREADS.pdf.

* cited by examiner

100

106

102

110

120

118

116

108

112

400 ⟍

402 ⟍

600

610 — Select a plurality of drill locations about a center of the craniotomy location 630 — Create a plurality of holes in the cranium 650 — Route, with the end mill, in a path corresponding with the plurality of drill locations

630

632 — Drill into the cranium

634 — Measure impedance through the end mill to the patient while drilling

636 — Measure axial force applied to the end mill while drilling

638 — Stop drilling in response to a change in the impedance or a change in axial force 640 — Record the final depth of the hole

800

810 — Connect an electrical contact to a subject

820 — Locate the outer surface of the cranium

830 — Drill down into the cranium

840 — Measure impedance through the end mill, the subject, and the electrical contact 850 — Gauge axial force of the end mill 860 — Stop drilling based upon a circuit that monitors changes in the impedance and axial force

AUTOMATIC CRANIOTOMY AND BONEWORK VIA MILLING, FORCE SENSING, AND IMPEDANCE SENSING

CROSS-REFERENCES TO RELATED APPLICATIONS

NOT APPLICABLE

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

1. Field of the Invention

The present invention is related to medical devices, systems, and methods, particularly for those involving bonework and milling in performing a craniotomy into a cranium of a patient. Embodiments of the disclosure include methods, devices, and control systems which may be utilized to perform a craniotomy.

2. Description of the Related Art

A craniotomy is a neurosurgical procedure of creating a surgical perforation of the cranium in order to access the intracranial structures (e.g. the brain). The procedure is often a time-consuming and high-risk procedure, in-part due to the reliance on manual cutting or drilling procedures to create the surgical perforation of the cranium. Present methods often involve the use of a number of handheld instruments, such as cranial perforator drills, cranial burrs, and an assortment of various cutting attachments. These instruments rely heavily on the skill of the technician or operator to successfully perform the craniotomy.

For a neural implant surgery, the nature of a craniotomy requires the perforation to be sufficiently close to the intracranial structures to provide access to the brain for subsequent electrode implantation. As such, operating manual equipment in such close proximity to the brain of a patient presents a variety of risks in causing damage to the intracranial structures, including the brain itself. Specifically, a craniotomy which exceeds the inner layer of cortical bone (the inner table) of the cranium and strikes the dura layer can cause damage or injury to the dura. Conversely, failure to perform the craniotomy deep enough into the cranium may result in an unsuccessful craniotomy by not providing sufficient access for a subsequent neurological implant.

Beyond safety risks, performing a craniotomy manually presents issues with consistency in the resulting perforation of the cranium. In particular, due to the curved shape of the cranium and irregular drilling surface, manual performance of a craniotomy presents concerns with both the dimensions of the perforation as well as the angle of the perforation relative the cranium surface. Neurological implant devices are typically not size adjustable and must securely fit within the craniotomy location to prevent the intracranial structures remaining exposed after implantation. As such, there is little tolerance for human-caused inaccuracies in the craniotomy procedure.

In addition, the process of performing a craniotomy manually is often extremely time consuming. Given the risks, including the safety of the patient as well as the high potential for failure, physicians or technicians generally perform the craniotomy slowly, with a great degree of care. Further, depending on the location of the craniotomy, geometric and anatomical limitations may further complicate the timeline of the procedure. Therefore, the craniotomy procedure presents a barrier to neurological implant procedures being available and affordable to more people, as a time-consuming surgery with a highly-skilled technician can be extremely costly and is limited by access to such qualified technicians.

In general, it would be advantageous to provide improved devices, systems, and methods to automate or semi-automate the craniotomy cutting process. Such improved techniques may avoid the shortcomings of manually performed craniotomies, including safety, accuracy, and cost.

BRIEF SUMMARY

The present invention generally provides improved devices, systems, and methods for performing a craniotomy or bone milling procedure. Embodiments of the present disclosure may utilize a computer automated milling tool, such as a computer numerical control ("CNC") machine to perform an automated or semi-automated craniotomy. In various aspects, the milling tool may be actuated, at least in-part, by instructions from a controller. The instructions may be based on input values received from sensors detecting bio-impedance of the patient and/or axial force applied between the working tip (e.g. end mill) and the cranium surface.

In one aspect, the system may include a CNC machine. The CNC machine may include an end effector, which is a movable component including a spindle and end mill. The spindle can be positioned relative to a craniotomy location on the cranium of a patient and is powered to rotate the end mill. The spindle may rotate the end mill at high speeds to provide smooth milling of the cranium. For example, the spindle may rotate the end mill at 1,000 to 150,000 revolutions per minute (rpm). In various embodiments the spindle may rotate the end mill at 60,000 revolutions per minute (rpm) or more. The end mill of the CNC machine may be of various sizes and shapes, as is appreciated by one skilled in the art. In some aspects, the end mill may be a router bit and may be capable of vertical drilling, side milling, or may be capable of performing both functions.

In various implementations, the end effector may be coupled to a movement mechanism, for example with a kinematic coupler. The movement mechanism may be a robotic system with one or more movement arms and one or more motors, which act to move the end effector in three dimensions. For example, the movement mechanism may include one or more servo motors that allow for rapid motion for positioning of the end mill, straight line motion in cutting, and circular motion.

In one aspect, the system may include a controller for controlling the milling parameters and positioning of the end mill. The controller may be connected with a processor, which in turn is connected with a memory. The processor acts to receive various inputs (discussed below) and to provide output parameters for operation of the end effector.

The outputs of the controller may include end mill positioning instructions (e.g. x-axis, y-axis, and z-axis coordinates), feed rate instructions, and spindle speed instructions. These outputs may include instructions for both face milling as well as plunge milling parameters. It should be understood that this list of output instructions is not exhaustive, and the processor may provide additional control parameters to the end effector and/or the end mill.

The memory may store various information significant to the milling parameters. This information may include stored parameters provided prior to the milling operation, or data compiled and received from various sensors of the milling system. For example, the controller may store input values provided by an operator (e.g. the physician), including pre-set information on the milling operation, including data on the cranium being milled. In various aspects, the memory may contain information provided from a scan or multiple scans of the cranium of the patient. For example, these scans may be provided from computed tomography ("CT"), ultrasound, fluoroscopy, or other similar scanning means. For example, these scans may be performed prior to the craniotomy operation and stored within the memory of the controller. The scanning information may, at least in-part, dictate the milling parameters provided to the end effector and end mill. In some aspects, the processor may provide input data received from various sensors during the milling operation to the memory. As such, the processor may access data from the memory for the duration of the milling operation and compare the stored data with live data.

In one aspect, the system may include input values from an impedance sensor. The impedance sensor may be a circuit including a power source (e.g. an AC power source), a supply contact (e.g. an anode), a return contact (e.g. a cathode), and a current detection resistor. The supply contact may be located on an electrically conductive surface of the spindle or end mill. For example, the supply contact may be located on a commutator brush of the spindle. The return contact may be positioned on tissue of the patient, such as on the lip of the patient. For example, the return contact may be attached to the lip of a patient with a lip clip.

The power source may apply a current, such as an alternating current, towards the supply contact in a monopolar orientation. The current may then conduct through the end mill of the end effector and through the tissue of the patient to the return contact, completing the circuit. As such, a measured "bio-impedance" encountered by the current flowing through the tissue of the patient may be measured. When the end mill first contacts the cranium surface, the current must pass through all layers of the cranium as it conducts to the return contact. Conversely, as the end mill goes deeper within the layers of the cranium, the layers for the current to pass through decreases, and as such the impedance lessens. Therefore, the impedance sensor may provide the processor with data indicating the position of the end mill relative to breaking through the inner layer of cortical bone (the inner table) of the cranium. By measuring the bio-impedance during the milling task, and storing the bio-impedance sensor data within the memory, the end mill may be stopped as it breaks through the inner layer of cortical bone. Such measuring of bio-impedance may limit or prevent damage to the dura layer. In some aspects, a change in bio-impedance indicating a breakthrough of the inner layer of cortical bone may trigger the processor to instruct the controller to stop milling into the cranium and/or to retract the end mill.

In one aspect, the system may include an axial force sensor, which acts to detect the amount of axial force applied to the workpiece (e.g. the cranium) by the end mill. In some aspects, this axial force sensor may be a shear beam load cell, which is incorporated within the end effector. An axial force sensor may utilize a spring to sense the force being applied to the workpiece (cranium). The axial force sensor may be electrically connected to the processor to provide the processor with input data on axial force being applied.

Information provided by the axial force sensor may indicate which layer of the cranium the end mill is currently milling through. As each layer of the cranium has varying density and strength characteristics, a harder portion of the cranium will produce higher axial force than a layer which is softer. As the end mill "breaks through" the inner layer of cortical bone of the cranium into the dura, the amount of force detected by the axial force sensor will rapidly decrease. As such, a change in the axial force may indicate the status of the milling operation. In some aspects, data provided by the axial force sensor may be provided to the processor, and may signal the controller to output a change in the milling parameters. In some aspects, a change indicating a breakthrough of the inner layer of cortical bone may trigger the controller to stop the milling into the cranium and/or retract the end mill.

In various implementations of the present disclosure, the memory may store axial force values for the duration of a milling action. The processor may then compare the current (live) axial force sensed by the axial force sensor to past axial forces applied during the current milling action. The processor may further calculate a maximum axial force detected during the milling action. In some aspects, when the axial force presently detected is less than the maximum axial force detected by a certain percentage or ratio, this may indicate that the end mill has broken through a layer of the cranium. For example, a drop to between 80% and 90% of the maximum axial force may indicate that the end mill has broken through the inner layer of cortical bone into the dura, and thus may indicate that the milling action is complete, in which point the processor may instruct the controller to stop the milling task and/or retract the end mill.

In one aspect, the system may include an optical assembly. The optical assembly may include an optical window and an optical mirror which are coupled to the end effector. The optical assembly may further include an optics protection shield. The optical assembly may direct light from the craniotomy location through the optical window to angularly reflect off the optical mirror. The light may be received from the optical mirror by a camera or other similar imaging device. For example, a camera optic stack may be positioned to receive the light from the craniotomy location to provide imagery of the craniotomy site and end mill. Such imagery may be used, for example, to position the end mill and/or monitor the progress of the milling operation, and provide adjustment of the milling parameters (if necessary).

In one aspect, the method for performing a craniotomy may include identifying a center of the desired craniotomy location. A plurality of borehole locations may be selected which are circumferentially located about the center of the craniotomy location. The CNC machine may then plunge mill through the layers of the cranium to a final depth at the plurality of borehole locations. The CNC machine may further perform a face milling operation in a mill path which connects the plurality of boreholes, such that an outer edge of the craniotomy is defined having the desired dimensions to ultimately receive the neurological implant. The CNC machine may adjust the depth at various points within the mill path based on the final depth of each borehole. After the mill path is completed, a remaining interior section of the craniotomy may remain which is detached from the remainder of the cranium, and may be subsequently removed, exposing the inner cranium.

Implementations of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to the entire specification of this patent, all drawings, and each claim.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

DETAILED DESCRIPTION

Implementations of the present disclosure are related to a device and system for performing a craniotomy having an automated milling machine and controller, and methods of use for the same.

In various implementations of the present disclosure, a craniotomy milling system may include a CNC machine, such as a CNC milling machine. The CNC machine includes both stationary and transient components. Specifically, the CNC machine may have a stationary base structure that may couple with one or more motors and actuator components which mechanically attach to an end effector via one or more control arms and act to control the positioning of the end effector. The end effector, as defined herein, represents the transient components of the CNC system, as described in further detail below.

Figure 1A:
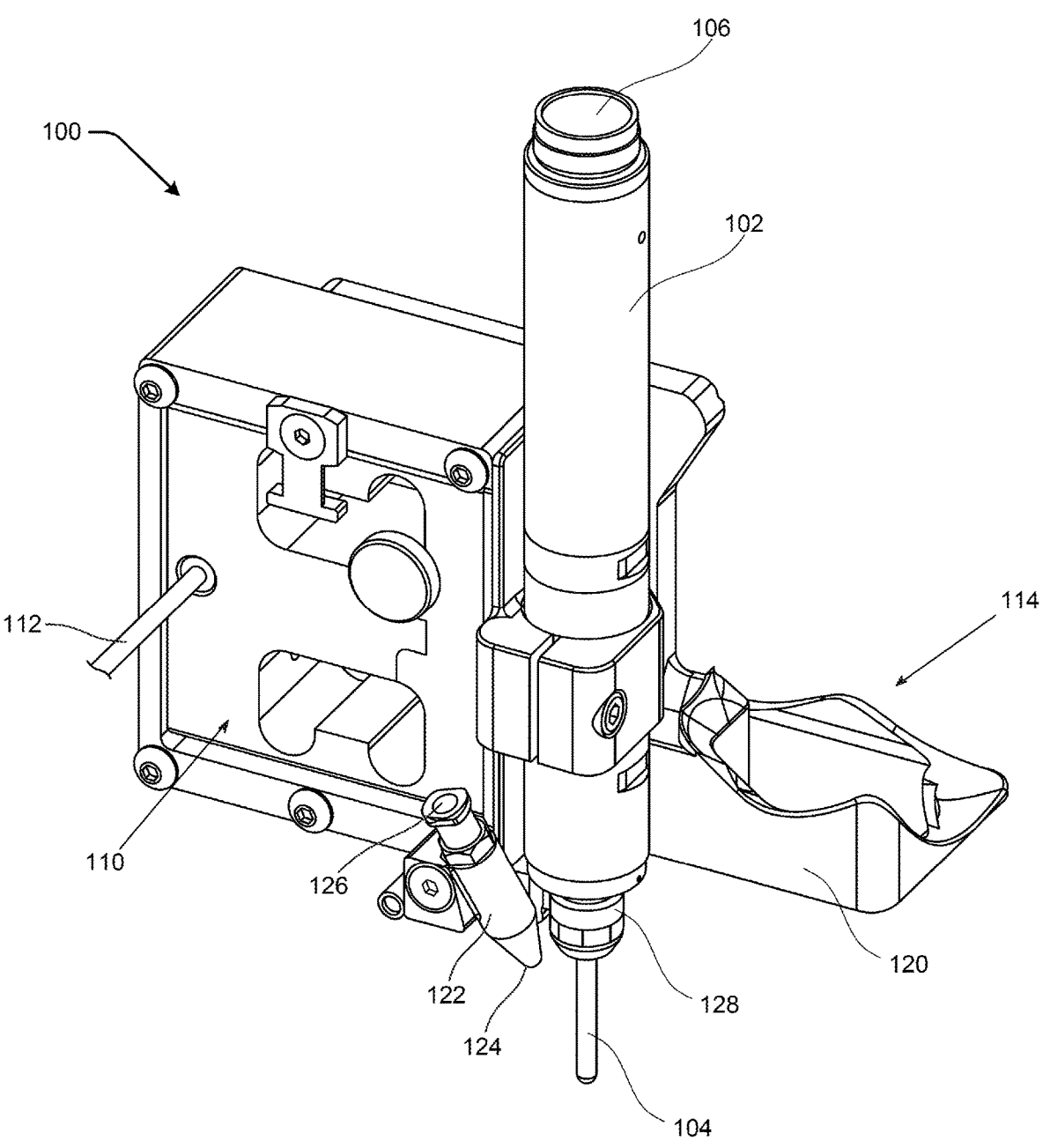
FIG. 1A illustrates a front perspective view of an end effector of a CNC machine according to implementations of the present technology.
Figure 1B:
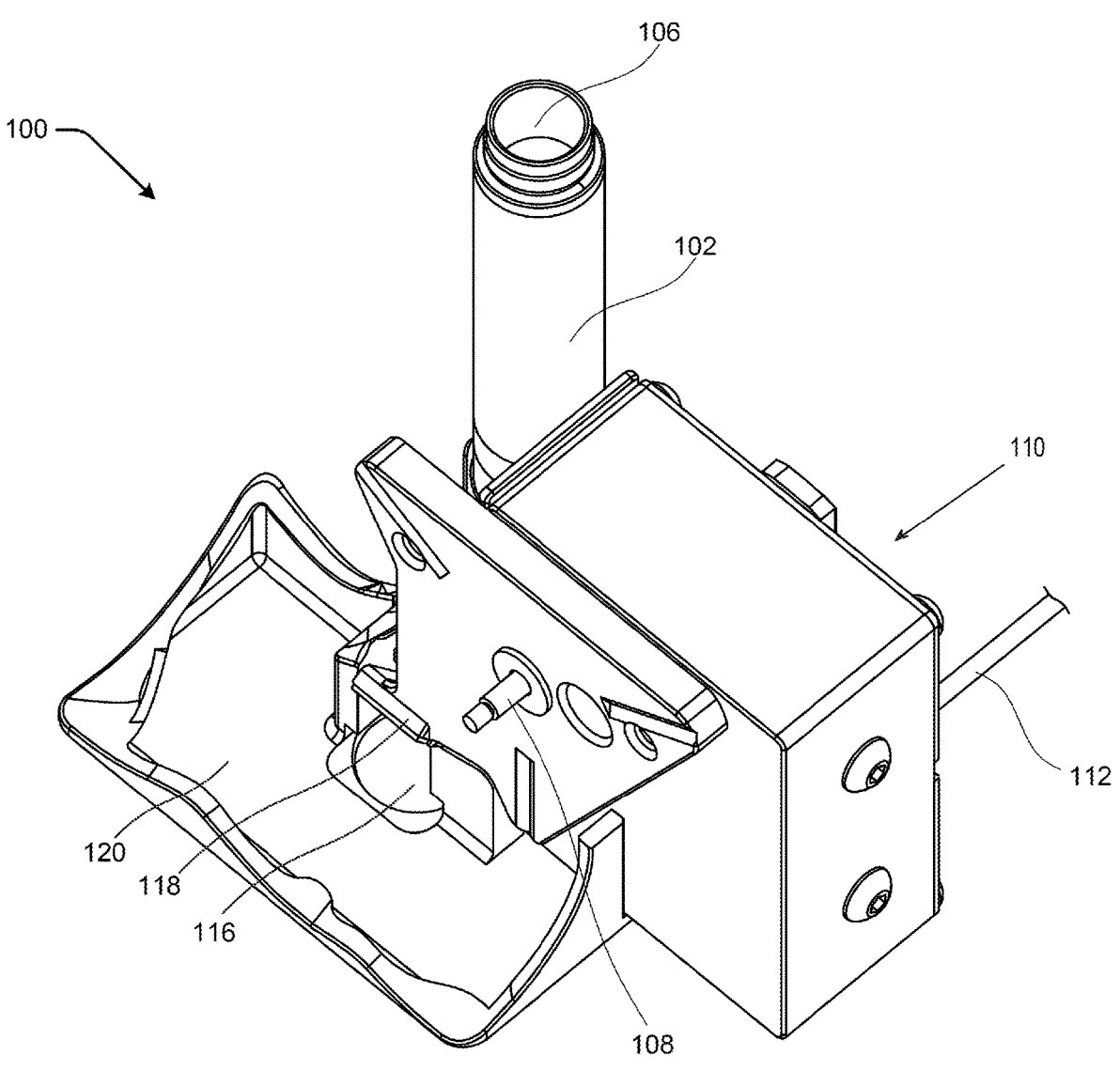
FIG. 1B illustrates a rear perspective view of the end effector of a CNC machine of FIG. 1A.

FIGS. 1A-1B show an end effector 100 of a craniotomy milling system. The end effector may include a spindle 102 which is motorized to spin the end mill 104. The spindle 102 may rotate the end mill 104 at 10,000 to 150,000 revolutions per minute (rpm). In various embodiments the spindle 102 may rotate the end mill 104 at 60,000 revolutions per minute (rpm) or more. In various embodiments, the spindle 102 may include a taper for holding tools, such that the end mill 104 may be automatically replaced (or swapped) for particular milling tasks. The spindle 102 may include a spindle connection port 106 which is configured to electrically connect the spindle 102 with the remainder of the craniotomy milling system, such as to receive power and control parameters (e.g. spindle speed).

The end mill 104 is a rotating cutting tool having a cylindrical shank with teeth. In various embodiments the end mill 104 can be shaped and configured from a variety of designs, including flat nose, ball nose, bull nose, and chambered. In various embodiments, the end mill 104 can be configured to both plunge mill (or drill) and face mill. In other embodiments, the end mill 104 can be configured to only plunge mill, such as being a drill bit. The end mill 104 may be of various dimensions, both in length and diameter to perform the desired milling task. Further, the spindle 102 may include a chuck or jaw configured to receive an end mill 104 of various sizes. The end mill 104 may be made of various materials to provide the desired cutting of the cranium. For example, the end mill 104 may be made from a biocompatible metal or metal alloy, for example, such as tungsten carbide, or other material including stainless steel and/or titanium, or may be of a metal or metal alloy coated with a biocompatible coating, such as a gold, copper, titanium (or titanium nitride, titanium carbo-nitride), chromium (and chromium nitride).

In various implementations, the end effector 100 may include a coupler 108 to attach the end effector 100 to the stationary components of the CNC machine, such as to one or more control arms. For example, the coupler 108 may be a kinematic coupler.

In various implementations, the end effector 100 may include an axial force sensor 110, which may act to detect the amount of axial force applied to the workpiece (e.g. the cranium) by the end mill 104. For example, the axial force sensor 110 may be a shear beam load cell. An axial force sensor 110 may utilize a spring to sense the force being applied to the workpiece (e.g. the cranium). In this way, the axial force sensor 110 can sense the hardness or material properties of the workpiece. The axial force sensor 110 may include a cable 112 to electrically connect the axial force sensor 110 with a controller.

In various implementations, the end effector 100 may further include an optical assembly 114. The optical assembly 114 may include various optical components including an optical window 116, at least one optical mirror 118, and an optics protection shield 120. The optical assembly 114 may direct light from the craniotomy location through the optical window 116 to angularly reflect off the optical mirror 118. The light may be received from the optical mirror 118 by a camera or other similar imaging device. For example, a camera optic stack may be positioned to receive the light from the craniotomy location to provide imagery of the craniotomy site and end mill. Such imagery may be used, for example, to position the end mill 104 and/or monitor the progress of the milling operation, and provide adjustment of the milling parameters (if necessary). For example, the camera or other imaging device may operably connect with the processor to provide information to the controller for positioning the end effector 100, as discussed below.

In various implementations, the end effector 100 may include a saline nozzle 122. A supply of saline may be provided through tubing which attaches to the inlet 126 of the saline nozzle 122. The saline may then be directed out of the saline nozzle 122 through the outlet 124 and directed towards the craniotomy location. Such saline application may provide cooling to the end effector 100 and/or the cranium and surrounding tissue. The saline application may also provide cleaning of the working area of the cranium to prevent or reduce blood or other biomaterials from compiling as the milling operation is performed.

In various implementations, the end effector 100 may include a commutator brush 128, which is coupled with the spindle 102, and may be positioned proximally with the end mill 104. A wire may be connected with the commutator brush 128, and the commutator brush 128 may allow electricity to be conducted from the wire to the end mill 104, while preventing the wire from rotating as the end mill 104 rotates. While described herein as an commutator brush 128, other mechanisms are contemplated which allow for electrical coupling with a rotating surface, and such mechanisms may similarly be implemented herein. In various implementations, the wire may be connected to non-rotating aspects of the spindle 102.

Figure 2:
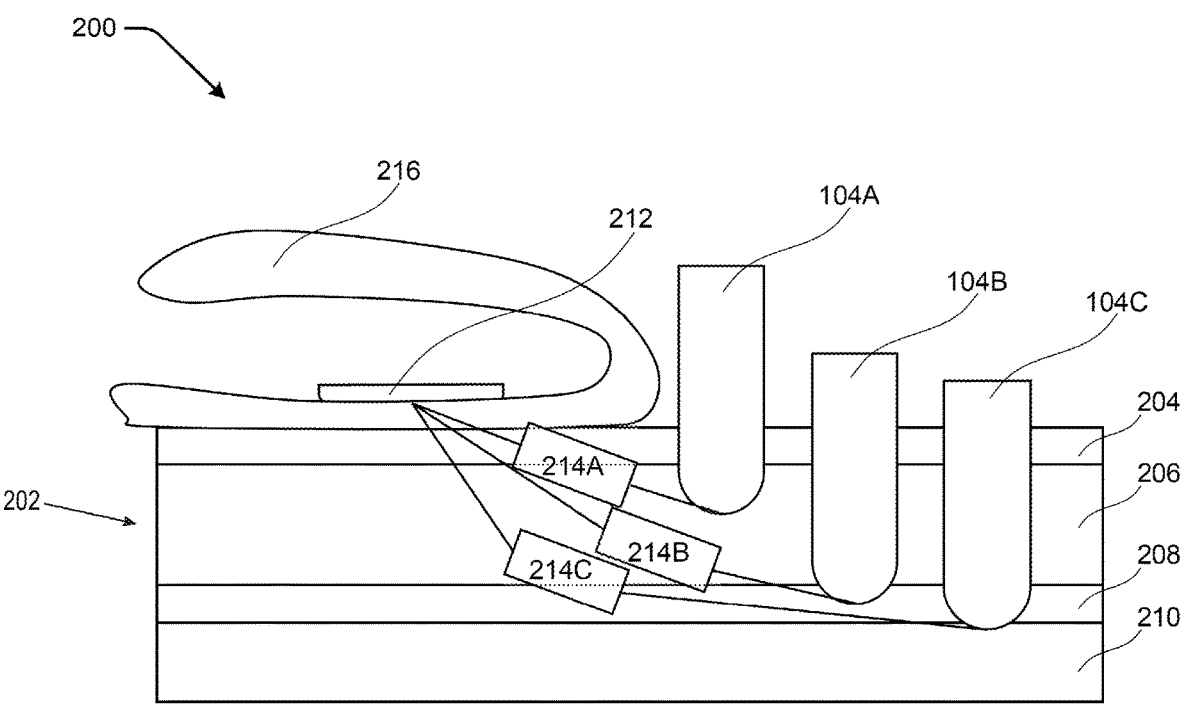
FIG. 2 is a diagram of measuring bio-impedance at various depths within the cranium according to implementations of the present technology.

FIG. 2 is a diagram of a bio-impedance measurement system 200. The system 200 shows cranium layers 202, including the outer layer of cortical bone 204, the cancellous bone 206, the inner layer of cortical bone 208, and the dura 210. As will be appreciated by one skilled in the art, the anatomy of the cranium includes various additional layers of biomaterial, including for example, the scalp and subcutaneous tissue, which are excluded from the figure for simplicity of discussion.

Each of the cranium layers 202 possess distinct material properties. For example, the outer layer of cortical bone 204 is relatively thick and tough, the cancellous bone 206 is a spongy, porous layer which may contain marrow and blood vessels, and the inner layer of cortical bone 208 is relatively thin and brittle compared to the outer layer of cortical bone 204. The dura 210 is a thick membrane. Further, the thickness and material properties of each of the cranium layers 202 may vary patient-by-patient, and further may vary across regions of the cranium.

The bio-impedance measurement system 200 may be a circuitry system. The system 200 may include a power source such as an A/C voltage source, configured in a monopolar configuration. The bio-impedance measurement system 200 may include a supply contact which electrically couples to the end mill 104. The supply contact may be a anode. In various embodiments the supply contact may be disposed in the commutator brush 128 of the end effector 100. In various implementations, the wire may be connected to non-rotating aspects of the spindle 102.

The bio-impedance measurement system 200 may conduct current through the end mill 104 and through tissue of the patient to a return contact 212. The return contact 212 may be a cathode. The return contact 212 may be placed at various locations on the patient, such as on the outer surface of the skin 216 of the patient. In various embodiments, the return contact may be attached to the outer or inner lip of the patient, such as with a lip clip. The bio-impedance measurement system 200 may further include a current detection device, such as a current detection resistor in a Wheatstone bridge. As such, the system 200 may measure the bio-impedance 214 encountered by the current as it passes through tissue of the patient. The bio-impedance measurement system 200 may be communicatively coupled with a processor (discussed below) to provide data of the bio-impedance 214 sensed. In general terms, as the depth of the end mill 104 within the cranium layers changes as a milling task is performed, the path in which the current travels from the supply contact (or from the end mill 104) to the return contact 212 changes, and as such the bio-impedance 214 recorded by the current detection device will change based on depth. Further, as each of the cranium layers 202 may have distinct material properties, each of the cranium layers 202 may have a distinct bio-impedance 214.

While discussed herein that bio-impedance 214 is a value reflective of the true impedance value for each of the cranium layers 202, it should be understood that the various components within the impedance measurement system 200, including for example the end mill 104, commutator brush 128, and/or return contact 212, may contribute the impedance sensed. As such, the bio-impedance measured 214 may be a scaled value to account for the impedance encountered by the various components of the bio-impedance measurement system 200. For example, the true (raw) impedance value measured for impedance may be adjusted by a constant value to reflect an adjusted (scaled) bio-impedance measurement. As discussed herein, a bio-impedance value may be either the true impedance value or the scaled bio-impedance value without departing from the teaching of the present disclosure.

FIG. 2 shows the end mill 104 at various depths in milling into the cranium layers 202. For example, end mill 104A has milled through the outer layer of cortical bone 204 and is milling within the cancellous bone 206. At this stage in the milling process, the bio-impedance measurement system 200 senses a first bio-impedance 214A associated with the depth of the end mill 104A within the cranium layers 202. Similarly, the end mill 104B has milled through the cancellous bone 206 and is milling within the inner layer of 208. At this stage in the milling process, the bio-impedance measurement system 200 senses a second bio-impedance 214B associated with the depth of the end mill 104B within the cranium layers 202. Finally, the end mill 104C has milled through (or is just beginning to mill through) the inner layer of the cortical bone 208 into the dura 210. At this stage in the milling process, the bio-impedance measurement system 200 senses a third bio-impedance 214C associated with the depth of the end mill 104C within the cranium layers 202. While the bio-impedance measurement system 200 is demonstrated as detecting a first bio-impedance 214A, a second bio-impedance 214B, and a third bio-impedance 214C, it should be understood that the bio-impedance measurement system 200 may continually or constantly measure the bio-impedance 214 at various depths of the milling process, and is not limited to a specific number of impedance measurements.

As discussed previously, the material properties of each of the cranium layers 202 may be distinct from each other. Further, dimensionally, with the return contact 212 maintaining a constant position, the distance between the end mill 104 and the return contact 212 will vary as the end mill proceeds deeper within the cranium layers 202. As such, the bio-impedance 214 sensed will change in relation to the dimensional and material property changes. For example, the outer layer of cortical bone 204 and inner layer of cortical bone 208 may be of hard, less conductive materials, and as such when the end mill 104 has plunge milled through these cranium layers, the bio-impedance 214 sensed will decrease. As the end mill 104 approaches the dura 210, the path for current to travel from the supply contact and return contact 212 are less impeded. In particular, the dura 210 often contains fluid, such as blood, resulting in lower impedance compared to other materials.

Figure 3:
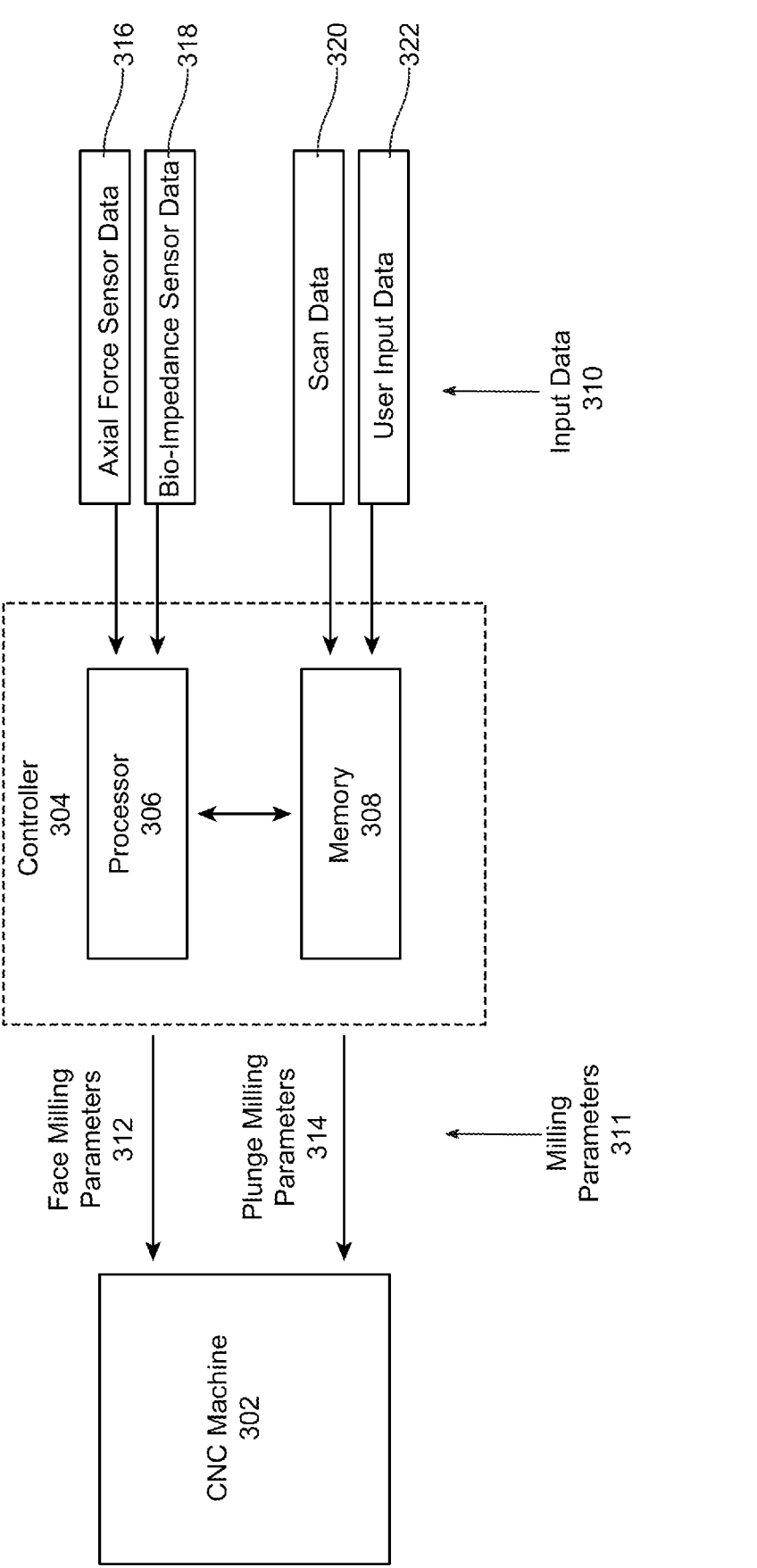
FIG. 3 an exemplary system architecture of a craniotomy milling system according to implementations of the present technology.

FIG. 3 shows an exemplary system architecture 300 for the craniotomy milling system. The system architecture may include a CNC machine 302, with components as described in FIGS. 1A-1B. The CNC machine 302 may be operably coupled with a controller 304. The controller 304 may be operably coupled with a processor 306 which may be operably coupled with a memory 308. The system architecture 300 may function such that the processor 306 receives input data 310 from one or more sources and from the memory, discussed below. The processor 306 may then calculate milling parameters based on the input data 310 and provide those milling parameters to the controller 304 to instruct operation of the CNC machine 302. For example, the controller 304 may transmit milling parameters 311, including for example, face milling parameters 312 for face milling tasks, and/or plunge milling parameters 314 for plunge milling tasks. Milling parameters 311 may include, but are not limited to, feed rate, rotation speed of the end mill 104, and location coordinates of the end effector 100.

In various implementations, one type of input data 310 the processor 306 may receive is axial force sensor data 316 from the axial force sensor 110. As discussed with respect to FIGS. 1A-1B, the axial force sensor 110 may be coupled to the processor 306 via the cable 112 and may provide the axial force sensor data 316 of the axial force experienced on the end mill 104 over the course of the milling task. The processor 306 may provide the axial force sensor data 316 to the memory 308 for the duration of the milling task. The memory 308 may further store historical information about known axial force measurements corresponding with various cranium layers 202, for example from past operations on other patients. Information provided by the axial force sensor 110 may indicate which of the cranium layers 202 (FIG. 2) the end mill 104 is currently milling through. The processor 306 may thus compare the most recently received axial force sensor data 316 from the axial force sensor 110 with stored data within the memory 308 from either past axial force sensor data from the same milling operation or task, historical data of axial-force values, or both. Using these comparisons, for example, the processor 306 may determine the depth of the end mill 104 within the cranium layers 202.

As each of the cranium layers 202 have varying density and strength characteristics, a harder portion of the cranium will produce higher axial force than a layer which is softer, as discussed previously. For example, because the dura 210 is a softer material than the inner layer of cortical bone 208, as the end mill 104 "breaks through" the inner layer of cortical bone 208 into the dura 210, the axial force detected by the axial force sensor 110 will rapidly decrease. As such, a change in the axial force sensed by the axial force sensor 110 may indicate the status of the milling task. In some aspects, the processor 306 may instruct the controller 304 to change the milling parameters 311 in response to the axial force sensor data 316 provided by the axial force sensor 110. In some aspects, a change in axial force indicating a breakthrough of the inner layer of cortical bone 208 may trigger the processor 306 to instruct the controller 304 to stop the CNC machine 302 milling into the cranium and/or retract the end mill 104.

In various implementations, the memory 308 may store axial force values for the duration of a milling action. The processor may then compare the current axial force sensed by the axial force sensor 110 to past axial forces applied during the current milling action. The processor 306 may further calculate a maximum axial force detected during the milling action. In some aspects, when the axial force presently detected is less than the maximum axial force detected by a certain percentage or ratio, this may indicate that the end mill 104 has broken through a layer of the cranium. For example, a current axial force detected by the axial force sensor 110 which is between 80% and 90% less than the maximum axial force in the current milling task may indicate that the end mill 110 has broken through the inner layer of cortical bone 208 into the dura 210, and thus may indicate that the milling action is complete. Similarly, the memory 308 may be programmed with a minimum predicted axial force value, such that when the axial force sensor data 316 received is less than the minimum predicted axial force value, the processor may determine that the milling action is complete. Upon determining the milling action is complete, the processor 306 may instruct the controller 304 to stop the milling task and/or retract the end mill 104.

In various implementations, the processor 306 may receive bio-impedance sensor data 318 from the bio-impedance measurement system 200. As discussed with respect to FIG. 2, the bio-impedance measurement system 200 may be a circuit which detects the bio-impedance measured between the supply contact, such as a component of the end effector 100, and return contact 212. As discussed previously, the specific material properties, including conductivity, of the cranium layers 202 may provide a unique bio-impedance between the supply contact and return contact 212. The bio-impedance measurement system 200 may provide the bio-impedance sensor data 318 which corresponds to the current bio-impedance detected between the supply contact and return contact 212. This bio-impedance sensor data 318 may be communicated to the memory 308 and stored for the duration of the milling task. The memory 308 may further store historical information about known bio-impedance corresponding with various cranium layers 202, for example from past operations on other patients. The processor 306 may thus compare the most recently received bio-impedance sensor data 318 from the bio-impedance measurement system 200 with stored data within the memory 308 from either past bio-impedance sensor data 318 from the same milling operation, historical data of bio-impedance values, or both. Using these comparisons, for example, the processor 306 may determine the depth of the end mill 104 within the cranium layers 202. As such, the processor 306 may determine a condition indicating that the end mill 104 has reached a desired final depth of the milling task, such as a breakthrough from the inner layer of the cortical bone 208 to the dura 210. In response to bio-impedance sensor data 318 from the bio-impedance measurement system 200, the processor 306 may provide an instruction to the controller 304 to change milling parameters 311, such as an instruction to the controller 304 to stop the milling task and/or retract the end mill 104.

In various implementations, the processor 306 may receive input data 310 from and stored within the memory 308. In one aspect, the memory 308 may be pre-programed with data specific to the current patient or milling operation. For example, the memory 308 may be programmed with scan data 320, compiled from a scan performed on the cranium of the patient prior to the craniotomy. The scan data 320 may be provided from, for example, a computed tomography ("CT") scan, ultrasound, fluoroscopy, or other similar scanning means.

In various implementations, the memory 308 may be programmed with user input data 322. The user input data 322 may be stored by an operator (e.g. a physician) prior to or during the craniotomy. The user input data 322 may include historical bio-impedance sensor data or historical axial force sensor data, as previously discussed, such as from known data values or results from previous craniotomy procedures. Such known data values may be provided as a range of values for each respective data type. For example, the memory 308 may be programmed with a predicted bio-impedance range for each of the cranium layers 202, including the outer layer of cortical bone 204, cancellous bone 206, the inner layer of cortical bone 208, and the dura 210. Similarly, the memory 308 may be programmed with a predicted axial force range for each of the cranium layers 202, including the outer layer of cortical bone 204, cancellous bone 206, the inner layer of cortical bone 208, and the dura 210.

The user input data 322 may include, for example, milling parameters 311 which are typical for a milling operation matching or similar to the current milling operation. As such, the processor 306 may have a starting framework of predicted milling parameters 311, and provide commands to the controller 304 to adjust the milling parameters 311. The user input data 322 may further include basic information on the parameters of the CNC machine 302, such as information regarding the type and size of the end mill 104.

In various implementations, the processor 306 may be programmed to compile and compare all of the input data 310 prior to providing a command to the controller 304 to change milling parameters 311. For example, axial force sensor data 316 indicating a breakthrough of the inner layer of cortical bone 208 may be compared to the bio-impedance sensor data 318 to determine whether both inputs suggest a condition requiring a change in milling parameters 311. In various embodiments, such comparisons of input data 310 may include comparison of any number of each of the types of input data 310. In this respect, each of the types of input data 310 may only in-part contribute to the processor 306 commanding a change in milling parameters 311. As such, the various input data 310 types provide confirmation of each other before a command is sent to the controller 304, to ensure that accuracy of the command.

In some aspects, each form of input data 310 may alone be conclusive for the processor 306 to command a change in milling parameters 311. For example, due to the inherent risks in plunge milling too deep into the cranium layers 202, the processor 306 may be programmed such that any one of the input data 310 received by the processor 306 is alone sufficient to command a change in milling parameters 311. For example, if the bio-impedance sensor data 318 indicates a condition requiring a stop to the milling task, that may alone be sufficient for the processor 306 to command the controller 304 to stop the CNC machine 302, regardless if the other input data 310 suggests that the milling parameters 311 continue. In this respect, the system architecture is a multi-fault tolerant system in that each of the input data 310 types are detecting the same condition (e.g. breaking through the inner layer of cortical bone 208), but by different means. As such, failure of one or more of the input data 310 to detect the condition leaves the remainder of the input data 310 types to continue to detect the same condition.

Figure 4:
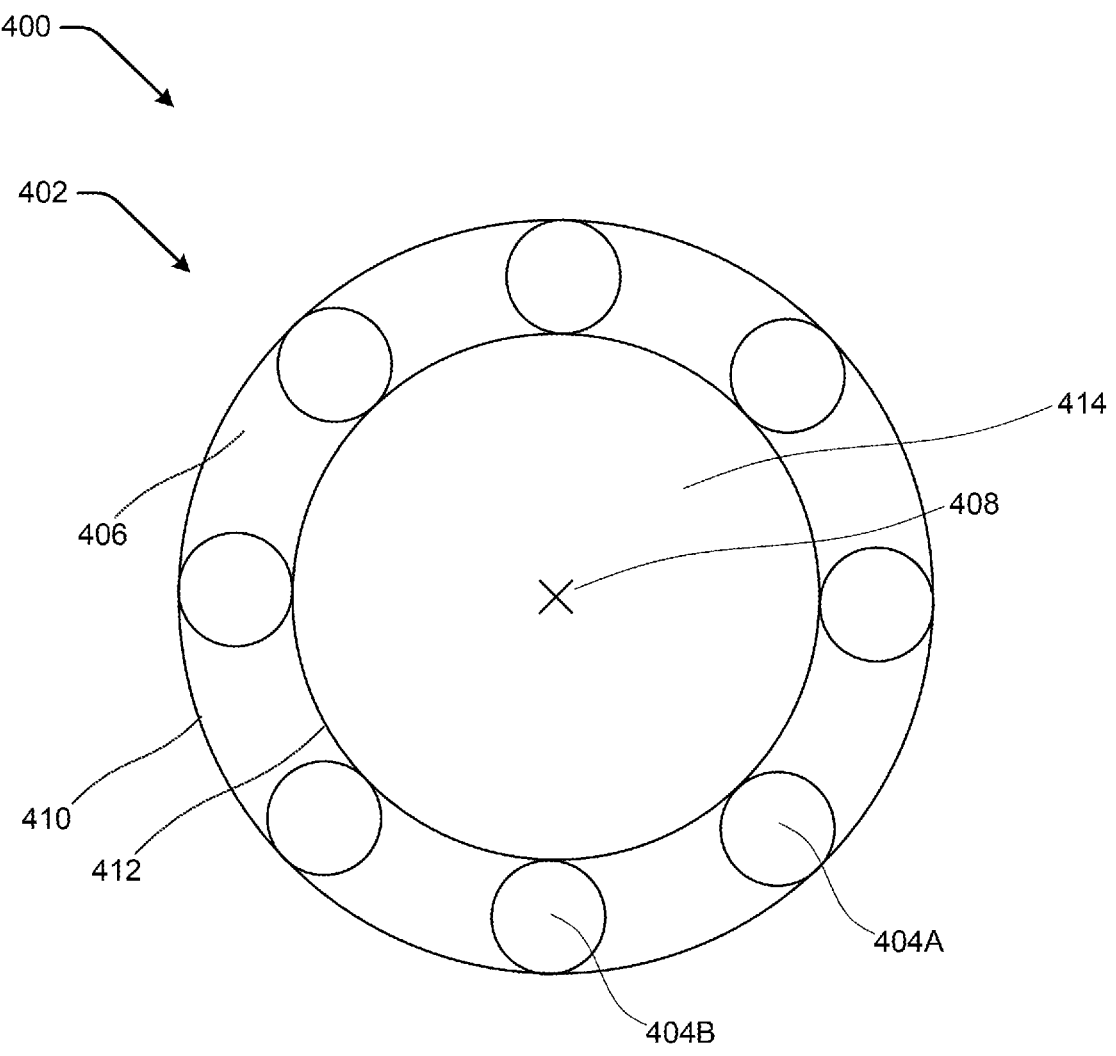
FIG. 4 illustrates a top view of an exemplary milling operation for performing a craniotomy according to implementations of the present technology.
Figure 5:
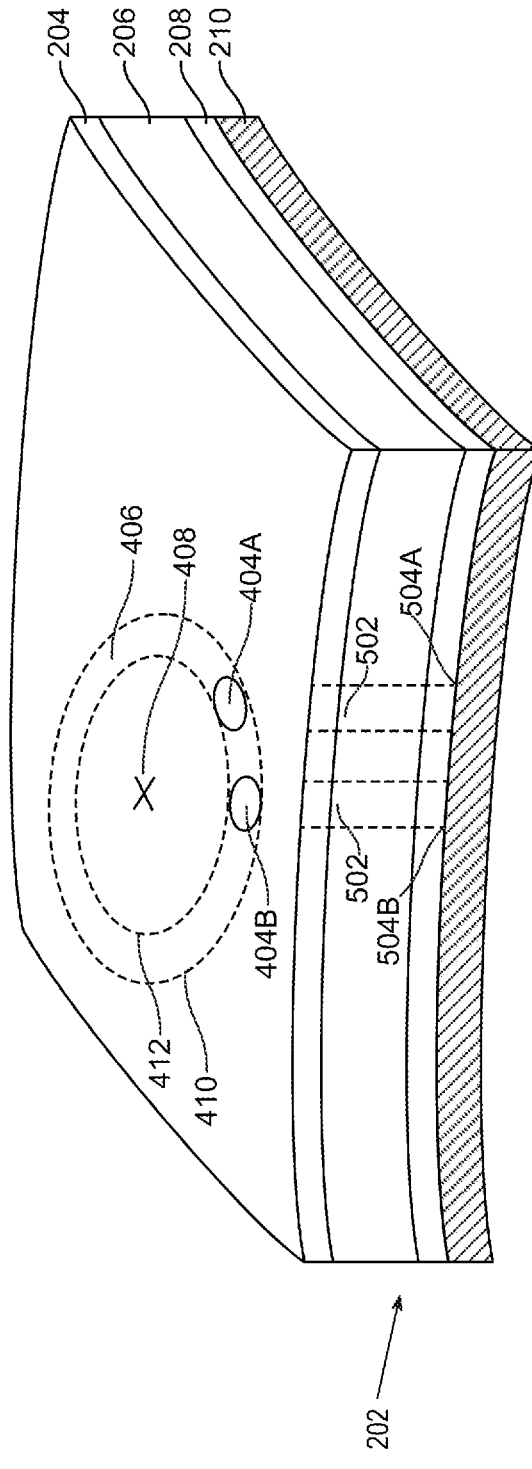
FIG. 5 illustrates a top perspective view of the exemplary milling operation of FIG. 4.

FIGS. 4-5 shows an exemplary milling operation 400 for performing a craniotomy at a craniotomy location 402. In one aspect, it may be advantageous for the milling operation 400 to be performed to include multiple milling tasks, including plunge milling one or more boreholes 404 and face milling an outline of the craniotomy location 402 along a face mill path 406. Providing multiple milling tasks within the milling operation 400 may allow greater precision and accuracy in performing the craniotomy, as the end mill 104 (FIG. 1) may be smaller than if the entire craniotomy was performed in a single plunge milling action. In addition, as the thickness of the cranium or cranium layers 202 (FIG. 2) may vary, a single milling action may not allow for varying the depth of the milling action at various locations at the craniotomy location 402.

The milling operation 400 may include first identifying a craniotomy center 408 (or centermark) of the craniotomy location 402. The craniotomy center 408 may be initially selected by an operator (e.g. a physician), and may be determined based on the desired location of the neurological implant following the craniotomy. In various embodiments, the starting position may be determined using the optical assembly 114. For example, the camera or other imaging device may provide imagery of the craniotomy location 402 to the processor 306, which may then provide instructions to the controller 304 to adjust the location of the end effector 100 based on the imagery. For further example, the craniotomy location 402 may be selected by the operator, and a visible marker may be placed at a craniotomy center 408 or other location of the craniotomy location 402. The camera or other imaging device may then image the visible marker and the processor 306 may provide instructions to the controller 308 to move the end effector 100 towards the visible marker. In various embodiments, an operator may store the starting position within the memory 308 (FIG. 3), such that the controller 304 provides instructions to the CNC machine 302 on the craniotomy center 408 to calibrate locations for the various milling actions. While the craniotomy center 408 is described as calibrating the CNC machine 302 as to the craniotomy location 402, it should be understood that various locations in or proximate to the craniotomy location 402 may be utilized in a similar matter, as would be appreciated by one skilled in the art.

The milling operation 400 may include plunge milling a plurality of boreholes 404. The boreholes 404 may be positioned circumferentially around the craniotomy center 408. The number of boreholes 404 may be pre-selected by the operator, and may include any number of boreholes 404, such as between 4 and 100 boreholes 404. Such pre-selected number of boreholes 404 may be stored as user input data 322 within the memory 308. The distance (radius) from the craniotomy center 408 to the boreholes 404 may be pre-selected by the operator. The outer edge of the boreholes 404 may ultimately correspond with the final dimensions of the craniotomy location 402, and thus selection of the distance from the craniotomy center 408 to the boreholes 404 may correspond with the desired final dimensions of the craniotomy.

In various implementations, the boreholes 404 may have a borehole path 502 extending vertically through the cranium layers 202 to a borehole final depth 504. For example, the borehole final depth 504 may be at the location the end mill 104 breaks through the inner layer of cortical bone 208. As described previously, the borehole final depth 504 may be determined by the processor 306 based for example on axial force sensor data 316, bio-impedance sensor data 318, scan data 320, and/or user input data 322, and provided to the CNC machine 302 via the controller 304. The borehole final depth 504 for each of the boreholes 404 may be stored in the memory 308.

In various implementations, the borehole path 502 and borehole final depth 504 may be the same for each of the boreholes 404. In other implementations, the borehole path 502 and borehole final depth 504 may vary for each of the boreholes 404. For example, the topography of the cranium layers 202 may vary across the cranium, and as such each borehole path 502 and borehole final depth 504 may depend, at least in part, of the topography of the cranium.

A face milling action may be performed by the CNC machine 302 along a face mill path 406. The face mill path 406 may correspond to the locations of the boreholes 404, and in various embodiments may act to "connect the dots" between the boreholes 404. The face mill path 406 may produce a mill path outer edge 410 and mill path inner edge 412. The mill path outer edge 410 may be the final outer edge desired for the craniotomy. The CNC machine 302 may face mill along the face mill path 406 according to the face milling parameters 312. In various implementations, the face milling parameters 312 may dictate the feed rate and depth at which the end mill 104 performs the milling task. For example, the end effector 100 of the CNC machine 302 may move to cut along the face mill path 406 in a plurality of rotations (passes), where each rotation around the face mill path 406 results in deepening the face mill path 406 deeper within the cranium layers 202.

In various implementations, the final depth of face milling may vary along the face milling path 406. The depth of face milling may correspond to the borehole final depth 504 of the boreholes 404. The borehole final depth 504 for each of the boreholes may be recalled by the processor 306 from the memory 308 to determine the depth of face milling at various locations in the face mill path 406. For example, the end mill 104 may be positioned to face mill the face mill path 406 to the borehole final depth 504A of borehole 404A when positioned at borehole 404A. As the end mill 104 advances towards borehole 404B, the depth of the end mill 104 may be adjusted such that the depth of the end mill 104 is at the borehole final depth 504B depth of borehole 404B when the end mill 104 is positioned at borehole 404B. The end mill 104 may continue to similarly adjust the depth as it advances to the remainder of the boreholes 404 until the face milling is completed. Such depth adjustment by the end mill 104 may be a linear adjustment, or other incremental adjustment in depth along the face mill path 406.

When completed to the desired depth, the face mill path may cut a ring-shaped perforation into the cranium, leaving an interior section 414 of cranium material. The interior section 414 may be fully separated from the remainder of the cranium. According to various implementations, the interior section 414 may be manually removed from the craniotomy location 402.

While the craniotomy location 402 is shown in the figure to be circular, it should be appreciated that the craniotomy location 402 may be of various shapes and dimensions without departing from the present disclosure. For example, the face mill path 406 may be an oval, rectangle, square, or other suitable shape, such as to match the dimensional requirements of a given neurological implant.

Figure 6:
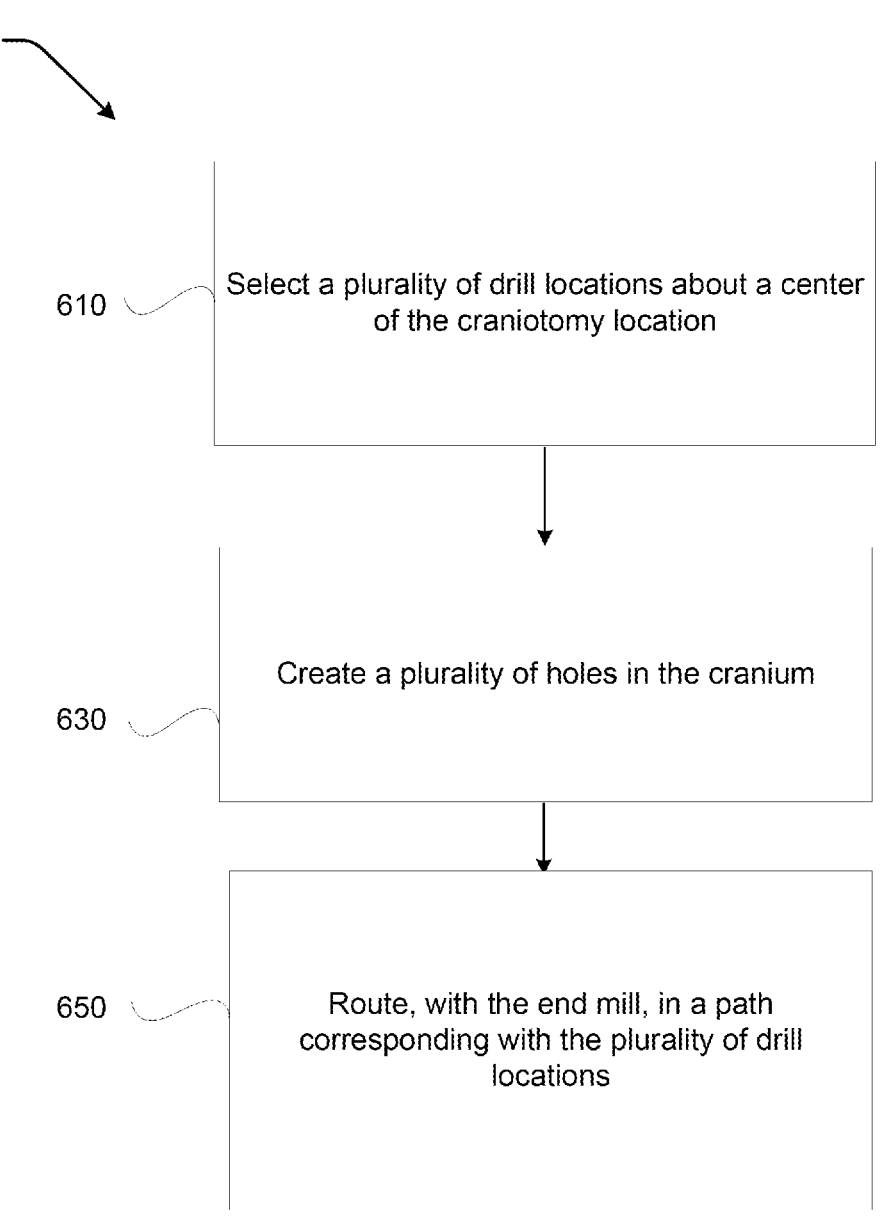
FIG. 6 illustrates a flowchart of an exemplary process for performing a craniotomy according to implementations of the present technology.

FIG. 6 is a flowchart of an exemplary process 600 for performing a craniotomy. In some implementations, one or more process blocks of the figure may be performed by a medical professional (e.g. a doctor, physician, or medical assistant), or other human. In some implementations, one or more process blocks of the figure may be performed by a computer controlled device, including for example an automated or semi-automated, computer controlled device (e.g. a robot).

At block 610, the process 600 may include selecting a plurality of plunge milling locations about a craniotomy center 408 (FIG. 4) of a craniotomy location 402. These plunge milling locations may be circumferentially located respective of the craniotomy center 408, and may further be equally spaced with respect to one another.

In various implementations, the process 600 may further include determining a starting location of a top surface of the cranium at the plurality of plunge mill locations. This may be performed for example by touching the end mill 104 (FIG. 1) to the surface of the cranium (without cutting) at each of the plunge mill locations. Further, the location of the cranium surface at each of the plunge mill locations may be stored, such as in the memory 308 (FIG. 3), for example as coordinates. The processor 306 may recall the starting location of the top surface of the cranium at each of the plurality of plunge milling locations, and provide instructions to the controller 304 to determine where the CNC machine should start plunge milling at each of the plurality of plunge milling locations.

At block 630, the process 600 may include creating a plurality of holes (e.g. boreholes 404) in the cranium. Block 630 is discussed in further detail with respect to FIG. 7.

At block 650, the process 600 may include face milling, with the end mill 104, in a path (e.g. face mill path 406 in FIG. 4) corresponding with the plurality of plunge milling locations (e.g. boreholes 404). The depth in which the face milling is performed may be determined, at least in part, by the final depths of the plurality of holes (e.g. borehole final depth 504 in FIG. 5). The face milling may create an outer edge of the craniotomy (e.g. mill path outer edge 410). The face milling may create an interior section 414 of cranium material located at the craniotomy center 408, wherein the interior section 414 of cranium material is removable such that an interior portion of the craniotomy is created.

Figure 7:
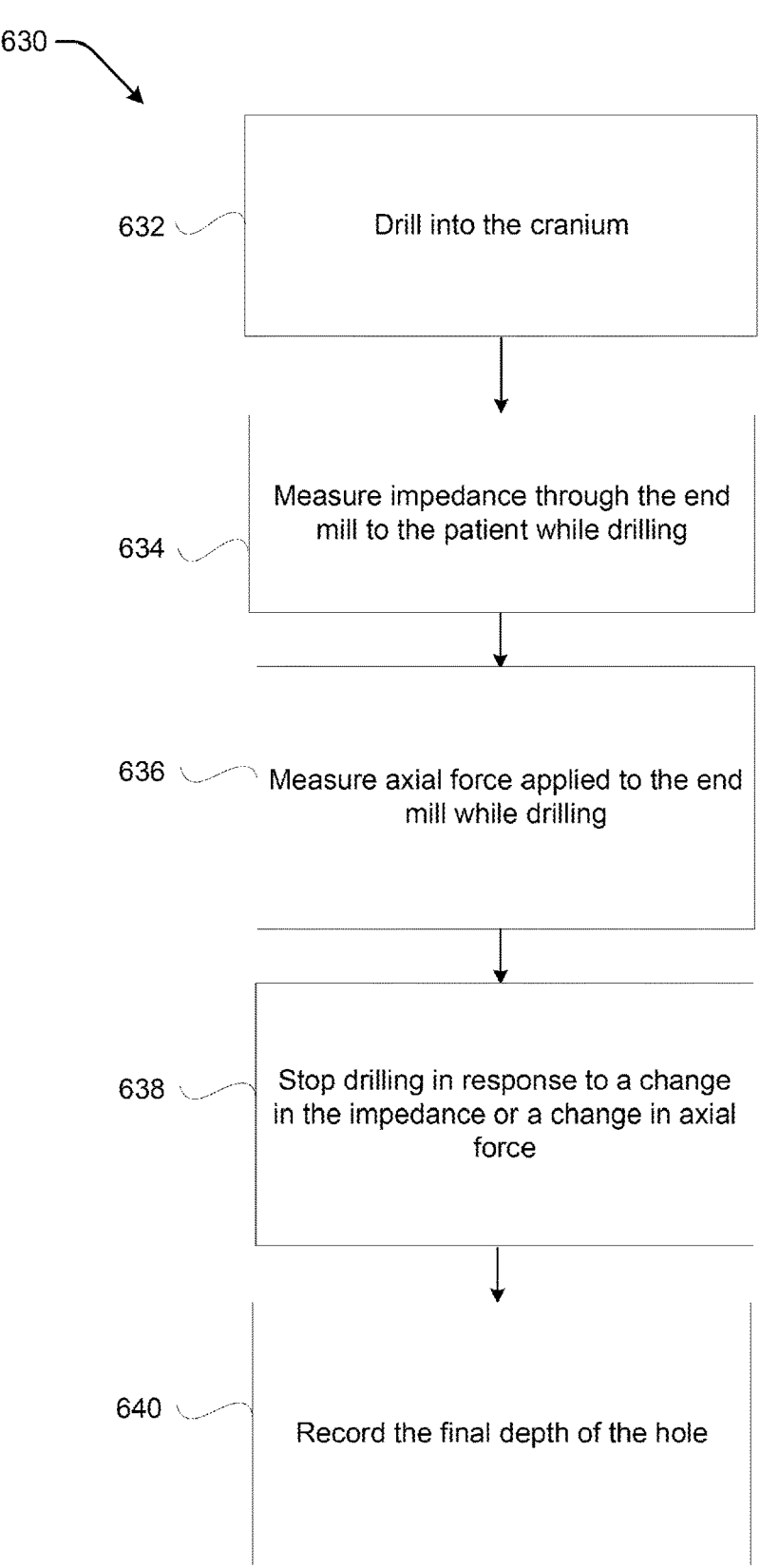
FIG. 7 illustrates a flowchart of an exemplary process of plunge milling a plurality of holes in the cranium according to implementations of the present technology.

FIG. 7 is a flowchart showing further details of creating a plurality of holes in the cranium at block 630 from the exemplary process 600. As discussed previously, the number of the plurality of holes may be determined by the operator (e.g. a physician) and may include 4 to 100 holes, such holes may be of the same or varying size.

At block 632, the process 600 may include plunge milling into the cranium, such as by plunge milling with an end mill 104 (FIG. 1). The plunge milling may be performed sequentially by the same end mill 104, or alternatively can be performed simultaneously or by selecting a different end mill 104 for one or more of the plunge milling, such as for size or the type of end mill 104. In addition, due to an end mill 104 becoming dull after one or more uses, the end mill 104 may be replaced between plunge milling each of the plurality of holes.

At block 634, the process 600 may include measuring impedance (e.g. bio-impedance) through the end mill 104 to the patient while plunge milling. In various aspects, the memory 308 of the controller 304 (FIG. 3) may be programmed with a predicted cortical impedance range indicative of the end mill 104 plunge milling in the inner layer of cortical bone 208. In various aspects, the memory 308 of the controller 304 may be programmed with a predicted cancellous impedance range indicative of the end mill 104 plunge milling in the cancellous bone 206 (FIG. 2). In various aspects, the memory 308 of the controller 304 may be programmed with a predicted dura impedance range indicative of the end mill 104 plunge milling in the dura 210. In various aspects, the predicted dura impedance range may be lower than the predicted cortical impedance range.

At block 636 the process 600 may include measuring axial force applied to the end mill 104 while plunge milling. The axial force may be measured using an axial force sensor 110, such as a shear beam load cell. In various implementations, the memory 308 of the controller 304 may be programmed with a predicted minimum axial force. In various implementations, measuring axial force applied to the end mill 104 while plunge milling may include determining a maximum axial force from the measured axial force, and storing the maximum axial force in the memory 308 of the controller 304.

In various implementations, the process 600 may include storing a predicted breakthrough ratio in the memory 308 of the controller 304, which measures a proportional difference between the maximum axial force and the measured axial force. The process 600 may include stopping plunge milling in response to the change in measured axial force due to the measured axial force being proportionally less than the maximum axial force by the predicted breakthrough ratio. For example, the predicted breakthrough ratio may be when the measured axial force is 80 to 90 percent less than maximum axial force.

At block 638 the process 600 may include stopping the plunge milling in response to a change in the impedance or a change in axial force. Stopping the plunge milling in response to a change in measured impedance may be due to the measured impedance being with a predicted dura impedance range. Stopping the plunge milling in response to a change in axial force may be due to the measured axial force being less than the predicted minimum axial force.

In various implementations, the process 600 may include measuring a predicted thickness of the cranium at the plurality of drill locations (e.g. boreholes 404 in FIG. 4) using computer tomography (CT) scanning. The predicted thickness of the cranium, for example from the CT scanning, may provide a prediction of the final depth of the respective hole (e.g. borehole final depth 504).

At block 640 the process 600 may include recording the final depth of the hole (e.g. borehole final depth 504). For example, the final depth of the hole may be stored in the memory 308 of the controller 304, and may be recalled by the processor 306 in face milling, with the end mill 104, in a path corresponding with the plurality of drill locations (block 650), such that the stored final depths of each of the holes may be associated or attribute to instructions to the CNC machine 302 for face milling along the face milling path 406.

Figure 8:
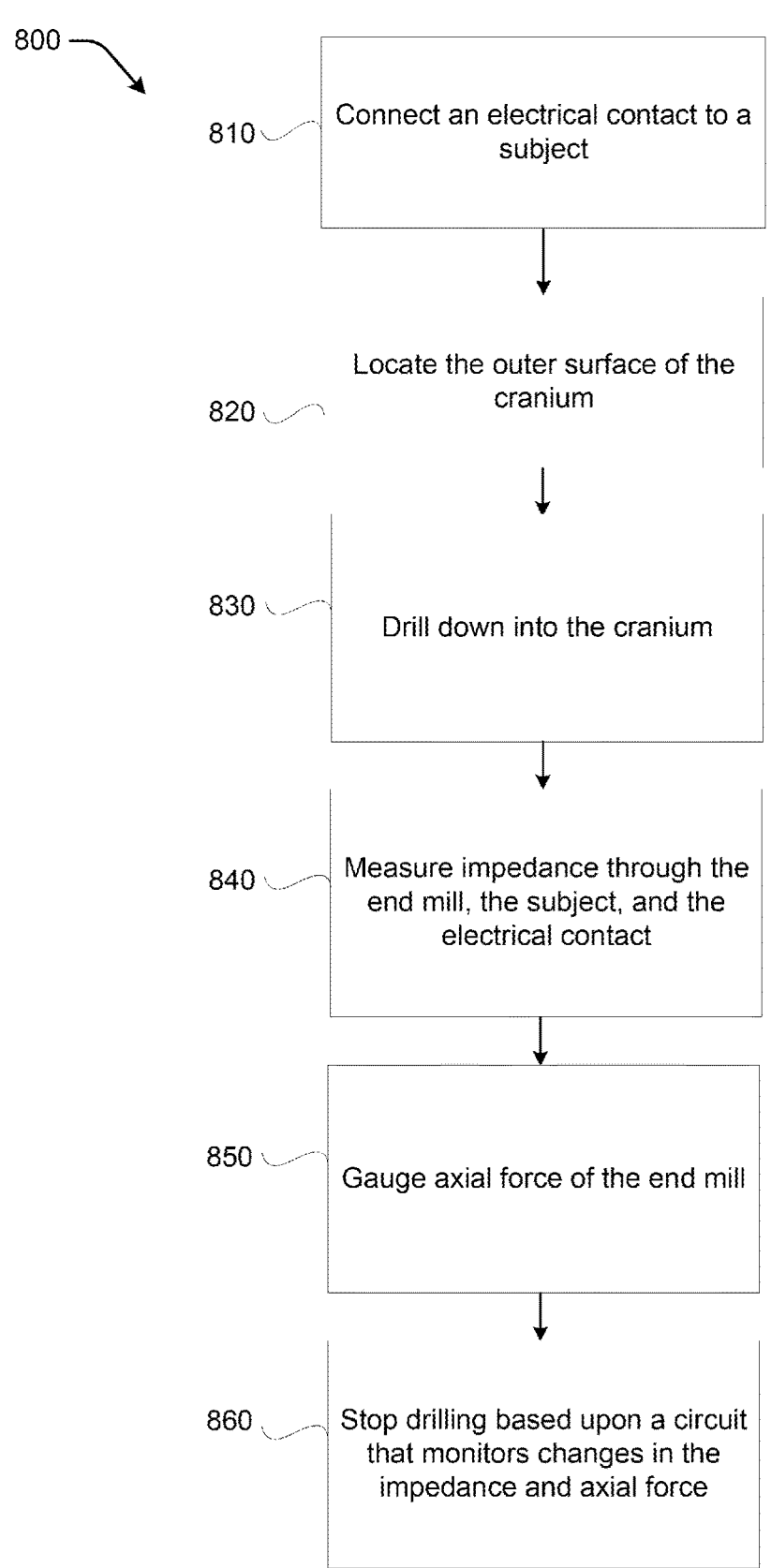
FIG. 8 illustrates a flowchart of an exemplary process for performing a craniotomy according to implementations of the present technology.

FIG. 8 illustrates a flowchart of an exemplary process 800 for performing a craniotomy. In some implementations, one or more process blocks of the figure may be performed by a medical professional (e.g. a doctor, physician, or medical assistant), or other human. In some implementations, one or more process blocks of the figure may be performed by a computer controlled device, including for example an automated or semi-automated, computer controlled device (e.g. a robot).

At block 810, the process 800 may include connecting an electrical contact (e.g. return contact 212 in FIG. 2) to a subject. The electrical contact may be electrically coupled to a computer numerical control (CNC) end mill (e.g. end mill 104 in FIG. 1). The electrical contact (e.g. return contact 212 of FIG. 2) may be removably connected to the exterior of a patient, such as on the skin 216 of the patient. In various implementations, the electrical contact may be incorporated in a lip clip and removably attached to the inner or outer surface of the lip (upper or lower) of a patient. The electrical contact may further be attached to the skin of the patient using an adhesive patch or sticker.

At block 820, the process 800 may include locating the outer surface of the cranium. This may be performed for example by touching the end mill 104 to the outer surface of the cranium (e.g. without cutting). In various implementations, locating the outer surface of the cranium may be performed manually (such as by an operator) by providing coordinates to the surface of the cranium or by manually adjusting the end mill 104 to the outer surface of the cranium. Further, the location of the outer surface of the cranium may be stored, such as in the memory 308. The processor 306 may recall the starting location of the outer surface of the cranium, and provide instructions to the controller 304 (FIG. 3) to determine where the CNC machine should start plunge milling.

At block 830, the process 800 may include plunge milling into the cranium from the outer surface with the end mill 104. In various implementations, plunge milling may be performed as described with respect to FIG. 7.

At block 840, the process 800 may include measuring impedance through the end mill 104, the subject, and the electrical contact during part of or the duration of plunge milling into the cranium. In various aspects, the processor 306 of the controller 304 may determine a bio-impedance by excluding the impedance of the end mill 104 and/or electrical contact. For example, user input data 322 may be provided to the memory 308 of the controller 304 regarding known values of the electrical contact and end mill. As such, the impedance value may be calibrated, such that it can be compared to known bio-impedance values of the cranium layers 202.

At block 850, the process 800 may include gauging the axial force of the end mill 104, such as during part or all of the plunge milling into the cranium. The axial force may be measured using an axial force sensor 110, such as a shear beam load cell. The axial force sensor 110 may be attached to the CNC machine 302, such as to the end effector 100 of the CNC machine 302.

At block 860, the process may include stopping plunge milling based upon a circuit that monitors changes in the impedance and axial force. The stopping may be determined either from a change in the impedance or the change in the axial force, or a combination of both a change in the impedance and a change in the axial force. The circuit may compare the impedance with stored impedance values indicative of respective layers of the cranium (e.g. cranium layers 202), such that plunge milling may be stopped based at least in-part upon the impedance indicating plunge milling to a desired depth within the cranium. In various aspects plunge milling may be stopped based at least in-part on impedance decreasing below a stored threshold impedance value, such as a stored threshold impedance value in a memory (e.g. memory 308) within the circuit.

The detailed description of example implementations refers to the accompanying drawings. The same reference numbers in different drawings may identify the same or similar elements. In the following description, for the purpose of explanation, numerous specific details are set forth in order to provide an understanding of various implementations of the subject matter. It will be evident, however, to those skilled in the art, that implementations of the inventive subject matter may be practiced without these specific details. In general, well-known structures and techniques are not necessarily shown in detail.

As will be apparent to those of skill in the art upon reading this disclosure, each of the individual implementations described and illustrated herein has discrete components and features which may be readily separated from or combined with the features of any of the other several implementations without departing from the scope or spirit of the present invention. Any recited method can be carried out in the order of events recited or in any other order that is logically possible.

It is understood that the examples and implementations described herein are for illustrative purposes and that various modifications or changes in light thereof will be suggested to persons skilled in the art and are to be included within the spirit and purview of this application and the scope of the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As used herein, "drill" or "drilling" may refer to vertical drilling operations, where the distal end of the end mill or bit is the active surface cutting through the working surface (e.g. the cranium or cranium layer). The terms "drilling" and "plunge milling" may refer to similar operations, distinguishable only by the type of machinery used. Similarly, in the context of plunge milling or drilling, "end mill" or "drill bit" may both refer to vertical drilling devices which may serve similar purposes. "Face milling" as used herein may refer to lateral cutting operations, where the side of the end mill or bit is the active surface cutting through the working surface (e.g. the cranium or cranium layer). The terms "face milling" and "routing" may refer to similar operations, distinguishable only by the type of machinery used.

As used herein "milling operation" may refer to the process of performing a craniotomy, including a plurality of face milling and plunge milling tasks. Conversely, a "milling task" may refer to a specific action taken as part of the milling operation. For example, a "milling task" may refer to the plunge milling of a specific hole.

It must be noted that as used herein and in the appended claims, the singular forms "a", "an", and "the" include plural referents unless the context clearly dictates otherwise. Although the terms "first", "second", etc. may be used herein to describe various elements, components, regions, layers and/or sections, it should be understood that they should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

What is claimed is:

1. A method of performing a craniotomy using a craniotomy system, which includes:
   a computer numerical control (CNC) milling machine including a spindle and an end mill, the spindle being positioned relative to a craniotomy location on a cranium of a patient, and
   a controller configured to control a feed rate of the end mill, the controller including a processor and a memory, the method comprising:

selecting a plurality of plunge mill locations being circumferentially located about a center of the craniotomy location;
   determining, by the craniotomy system, an estimated final depth of a hole to be formed at each of the plurality of plunge mill locations based on a medical image of the cranium of the patient;
   creating a plurality of holes in the cranium, each hole created by:
      plunge milling into the cranium at a respective plunge mill location of the plurality of plunge mill locations;
      measuring an impedance through the end mill to the patient while plunge milling;
      measuring an axial force applied to the end mill while plunge milling;
      calculating a predicted breakthrough ratio;
      stopping the plunge milling in response to a change in the impedance or in response to a change in the axial force, wherein the stopping the plunge milling in response to the change in the axial force is due to the axial force being proportionally less than a maximum axial force by the predicted breakthrough ratio; and
      storing the estimated final depth of the respective hole in the memory of the controller; and
   face milling, with the end mill, in a path corresponding to the plurality of plunge mill locations to create an outer edge of the craniotomy, wherein a cutting depth at a plurality of points of the path is determined at least in part by the estimated final depths of the plurality of holes.

2. The method of claim 1, further comprising:
   determining a starting location of a top surface of the cranium at the plurality of plunge mill locations by positioning the end mill concentric with the respective plunge mill location and touching, without cutting, the end mill against the cranium at the respective plunge mill location.

3. The method of claim 2, further comprising:
   storing the starting location of the top surface of the cranium at the plurality of plunge mill locations in the memory of the controller.

4. The method of claim 1, wherein the memory of the controller is programmed with a predicted cortical impedance range indicative of the end mill plunge milling in an inner layer of cortical bone of the cranium and a predicted dura impedance range indicative of the end mill plunge milling in dura of the cranium.

5. The method of claim 4, wherein the memory of the controller is programmed with a predicted cancellous impedance range.

6. The method of claim 4, wherein stopping the plunge milling in response to the change in the measured impedance is due to the measured impedance being within the predicted dura impedance range.

7. The method of claim 6, wherein the predicted dura impedance range is lower than the predicted cortical impedance range.

8. The method of claim 1, wherein the memory of the controller is programmed with a predicted minimum axial force, wherein stopping the plunge milling in response to the change in the measured axial force is due to the measured axial force being less than the predicted minimum axial force.

9. The method of claim 1, further comprising:

determining a maximum axial force from the axial force;

storing the maximum axial force in the memory of the controller; and storing the predicted breakthrough ratio in the memory of the controller, the predicted breakthrough ratio measuring a proportional difference between the maximum axial force and the axial force.

10. The method of claim 9, wherein the predicted breakthrough ratio is between 80% and 90%.

11. The method of claim 1, wherein face milling with the end mill creates an interior section of cranium material located at the center of the craniotomy location, wherein the interior section of cranium material is removable such that an interior portion of the craniotomy is created.

12. The method of claim 1, further comprising:

obtaining a computed tomography (CT) scan of the cranium of the patient as the medical image.

13. The method of claim 1, further comprising:

storing the estimated final depth of the hole to be formed at each of the plurality of plunge mill locations in the memory of the controller.

14. The method of claim 13, wherein the creating the plurality of holes in the cranium by plunge milling into the cranium further comprises recalling the estimated final depth of the hole to be formed, and the stopping the plunge milling in response to the change in the measured impedance or the change in the measured axial force further comprises stopping the plunge milling in response to plunge milling the estimated final depth into the cranium.

15. The method of claim 1, wherein the impedance is measured via an impedance measurement system electrically coupled to the CNC milling machine and the controller.

16. The method of claim 15, wherein the impedance measurement system includes a first electrical contact in the end mill and a second electrical contact configured to be removably coupled to the patient, and the impedance is measured between the first electrical contact and the second electrical contact.

17. The method of claim 1, wherein the axial force is measured via an axial force sensor electrically coupled to the CNC milling machine and the controller.

18. The method of claim 1, further comprising:

determining, optically via an optical assembly, the center of the craniotomy location through an optical window of the optical assembly, the optical assembly being attached to the CNC milling machine.

19. A method of performing a craniotomy, comprising:

connecting an electrical contact to a subject, the electrical contact being electrically coupled to a computer numerical control (CNC) end mill;

locating an outer surface of a cranium of the subject;

determining an estimated final depth of a hole to be formed at a target plunge mill location based on a medical image of the cranium of the subject;

plunge milling into the cranium from the outer surface with the end mill at the target plunge mill location;

measuring, during the plunge milling, an impedance through the end mill, the subject, and the electrical contact;

gauging, during the plunge milling, an axial force of the end mill; and stopping the plunge milling based upon a circuit that monitors changes in the impedance simultaneously with changes in the axial force, wherein the changes in the axial force are determined by the axial force being proportionally less than a maximum axial force by a predicted breakthrough ratio.

20. A method of performing a craniotomy using a craniotomy system, which includes a computer numerical control (CNC) milling machine including a spindle and an end mill, the spindle being positioned relative to a craniotomy location on a cranium of a patient, and a controller configured to control a feed rate of the end mill, the controller including a processor and a memory, the memory of the controller being programmed with a predicted cortical impedance range indicative of the end mill plunge milling in an inner layer of cortical bone of the cranium and a predicted dura impedance range indicative of the end mill plunge milling in dura of the cranium, the method comprising:

selecting a plurality of plunge mill locations being circumferentially located about a center of the craniotomy location;

creating a plurality of holes in the cranium, each hole created by:

plunge milling into the cranium at a respective plunge mill location of the plurality of plunge mill locations;

measuring an impedance through the end mill to the patient while plunge milling;

measuring an axial force applied to the end mill while plunge milling;

stopping the plunge milling in response to a change in the impedance or in response to a change in the axial force; and storing a final depth of the respective hole in the memory of the controller; and face milling, with the end mill, in a path corresponding to the plurality of plunge mill locations to create an outer edge of the craniotomy, wherein a cutting depth at a plurality of points of the path is determined at least in part by the final depths of the plurality of holes.

* * * * *